United States Patent [19]
Sievert

[11] Patent Number: 5,944,981
[45] Date of Patent: Aug. 31, 1999

[54] PYROLYSIS FURNACE TUBES

[75] Inventor: James Bernard Sievert, Katy, Tex.

[73] Assignee: The M. W. Kellogg Company, Houston, Tex.

[21] Appl. No.: 08/958,825

[22] Filed: Oct. 28, 1997

[51] Int. Cl.[6] .............................. C10G 9/12; C10G 9/14; C07C 4/04
[52] U.S. Cl. ..................... 208/48 R; 208/132; 422/240; 422/241; 585/648; 585/920
[58] Field of Search .................. 208/48 R, 132; 422/240, 241; 585/648, 920

[56] References Cited

U.S. PATENT DOCUMENTS

| | | | |
|---|---|---|---|
| 3,531,394 | 9/1970 | Koszman | 208/48 |
| 5,446,229 | 8/1995 | Taylor et al. | 585/648 |

*Primary Examiner*—Glenn Caldarola
*Assistant Examiner*—Tam M. Nguyen
*Attorney, Agent, or Firm*—The M. W. Kellogg Company

[57] ABSTRACT

An improved method for cracking a hydrocarbon feedstock comprising passing the feedstock through furnace tubes at high temperatures. The improvement comprises tubes comprised of a nickel-cobalt alloy containing: nickel; 27.0–33.0 weight percent cobalt; 26.0–30.0 weight percent chromium; 2.4–3.0 weight percent silicon; 0.20–0.80 weight percent titanium; not more than 3.5 weight percent iron; not more than 1.5 weight percent manganese; not more than 1.0 weight percent columbium; not more than 1.0 weight percent molybdenum; not more than 1.0 weight percent tungsten; not more than 0.15 weight percent carbon; not more than 0.030 weight percent phosphorus; and not more than 0.015 weight percent sulfur. The improvement results in lower coking rates inside the furnace tubes, thus enhancing furnace efficiency and tube life.

7 Claims, No Drawings

PYROLYSIS FURNACE TUBES

FIELD OF THE INVENTION

The subject invention is related to a pyrolysis furnace for the pyrolysis of hydrocarbons. More specifically the subject invention is related to the use of nickel-cobalt-chrome-silicon alloy furnace tubes to reduce coking therein.

BACKGROUND OF THE INVENTION

Pyrolysis in the tubes of a furnace or thermal reactor accounts for almost all of the ethylene produced today. The feedstock properties and the furnace operating conditions dictate the effluent composition. To produce the desired product the reaction is performed at high temperatures (approximately 750° to 1100° C.). For some designs, higher reaction yields occur using relatively short residence times (0.05 to 0.6 seconds) and relatively small diameter tubes and relatively low hydrocarbon partial pressures. During pyrolysis the hydrocarbons break down and liberate carbon in the form of soot or coke. Over time this carbon results in the process of carburization of the tube inner radius; wherein carbon enters the metal and combines with chrome. Carburization can increase the hardness of the tubes making them more brittle and more susceptible to stress fractures. This is accompanied by an increase in forces within the tube metal due to volume expansions resulting from chromium carbide formations.

During its operating lifetime a furnace is subject to multiple shutdowns and startups which impose cyclic thermal stresses on the furnace tubes. The severity of the operating conditions are such that the furnace tube material can withstand a finite number of cycles before experiencing a failure. These can be characterized as a localized stress fracture or as catastrophic failures. The occurrence of carburization reduces the number of cycles the furnace tube material can withstand.

The liberation of the carbon atoms during pyrolysis also results in coke formation which can deposit onto the inside of the reactor tubes and eventually cause fouling. This decreases furnace heat transfer and effectiveness. At some point it is necessary to shut down the furnace for decoking the furnace tubes. These shutdowns not only cause the thermal stresses noted above, but are also very costly and time consuming. For example, a single shutdown can cost the producer hundreds of thousands of dollars. Thus, it is even more desirable to minimize the furnace tube coking rate. Therefore, it would be desirable to utilize a furnace tube material that experiences minimal coking and minimal carburization.

The selection of furnace tube alloys is complicated by competing factors. Certain elements such as iron, cobalt, and nickel improve physical properties but are generally considered to accelerate or catalyze the coking reaction, so it is generally desired to avoid using these as components in the furnace tube alloy. Other elements, such as silicon are known to inhibit coking during pyrolysis conditions, but adversely affect the physical properties of the alloy. Silicon, for example, would require use in such high alloy proportions that the resulting alloy would be unsuitable for furnace use since that alloy would not be weldable.

SUMMARY OF THE INVENTION

The present invention is directed to an improvement in the pyrolysis of hydrocarbons that minimizes coking and improves the resistance to carburization of associated tubing metals. More specifically the present invention is directed to an improvement in the method for cracking a hydrocarbon feedstock comprising passing the feedstock through tubes running through a furnace at an elevated temperature. The improvement is that the tube material is comprised of a nickel-cobalt-chrome-silicone alloy comprising: nickel (balance); 27.0–33.0 weight percent cobalt; 26.0–30.0 weight percent chromium; 2.4–3.0 weight percent silicon; 0.20–0.80 weight percent titanium; not more than 3.5 weight percent iron; not more than 1.5 weight percent manganese; not more than 1.0 weight percent columbium (niobium); not more than 1.0 weight percent molybdenum; not more than 1.0 weight percent tungsten; not more than 0.15 weight percent carbon; not more than 0.030 weight percent phosphorus; and not more than 0.015 weight percent sulfur.

Another aspect of the invention is directed to a method for cracking a hydrocarbon feedstock comprising passing the feedstock through tubes running through a furnace at an elevated temperature where the tube material is comprised of the nickel-cobalt-chrome-silicon alloy and the feedstock is ethane.

An additional aspect of the invention is directed to a method for cracking a hydrocarbon feedstock comprising passing the feedstock through tubes running through a furnace at an elevated temperature where the tube material is comprised of the nickel-cobalt-chrome-silicon alloy and the feedstock is naphtha.

A further aspect of the invention is directed to a method for cracking a hydrocarbon feedstock comprising passing the feedstock through tubes running through a furnace at an elevated temperature where the tube material is comprised of the nickel-cobalt-chrome-silicon alloy where the approximate elevated temperatures range from 750° C. to 1100° C.

DETAILED DESCRIPTION

The pyrolysis furnace used in the method of the present invention is constructed according to pyrolysis furnace construction techniques well known in the art, except that a special nickel-cobalt-chrome-silicon alloy is used for the fabrication of the furnace tubes. The pyrolysis furnace tube material of the present invention is comprised of a nickel-cobalt alloy that experiences surprisingly low coking on its surface upon exposure to a pyrolysis environment. More specifically the composition of the nickel-cobalt alloy is: nickel (balance); 27.0–33.0 weight percent cobalt; 26.0–30.0 weight percent chromium; 2.4–3.0 weight percent silicon; 0.20–0.80 weight percent titanium; not more than 3.5 weight percent iron; not more than 1.5 weight percent manganese; not more than 1.0 weight percent columbium; not more than 1.0 weight percent molybdenum; not more than 1.0 weight percent tungsten; not more than 0.15 weight percent carbon; not more than 0.030 weight percent phosphorus; and not more than 0.015 weight percent sulfur. Although not intending to be bound by theory, it is believed that the iron content should be as low as possible to inhibit coking, preferably less than 1 weight percent and particularly less than about 0.5 weight percent of the alloy. The alloy is available commercially, for example, from Haynes International of Kokomo, Ind. under the trade designation HR160. One method of fabrication is to produce the alloy as a flat plate that is then formed and welded into furnace tubes, but the alloy can also be produced into a seamless tube by extrusion or drawing the material through a die. Moreover, whatever method is used, the material can be produced and fabricated in accordance with the requirements of the ASME Boiler and Pressure Vessel Code, Section VIII, Division 1.

The operation of the pyrolysis furnace is conducted in the usual manner according to well known methodology, but with the major exception that operating periods and total feedstock throughput between decoking cycles are significantly increased owing to the substantially lower coking rates of the furnace tubes. As a direct result, the efficiency (conversion rates) of the furnace tubes stay high for a longer period of time because of less fouling, and at the same time the life of the furnace tubes can be expected to be much longer due to less frequent decoking than furnace tubes heretofore available. Thus fewer thermal stress cycles are experienced by the tubes.

The furnace is operated using typical pyrolysis feedstocks such as, for example, ethane, naphtha and the like. Typical pyrolysis furnace operating conditions include those well known in the art, for example, temperatures ranging from 750° C. to 1100° C., residence times from 0.05 to 0.6 seconds, and relatively low hydrocarbon partial pressures such as below 20–30 psia. The downstream processing of the effluent uses conventional equipment and methodology, e.g. transfer line exchanger and/or quench exchanger, olefins distillation and recovery, etc.

The present invention is further illustrated by the following example:

EXAMPLE 1

The low coking experienced by the nickel-cobalt-chrome-silicon alloy (HR160) of the present invention was observed after numerous bench test studies. The bench test studies also analyzed quartz, a nickel-chromium alloy (230), and a nickel-chrome-iron alloy (800H). These HR160 and alloy 230 materials were obtained from Haynes International; whereas the 800H was supplied by Sumitomo or INCO International. The composition of the three alloys is illustrated in Table 1.

TABLE 1

| | Analyses | | |
|---|---|---|---|
| | | Alloys | |
| Elements | HR 160 | 230 | 800H |
| Si | 1.8 | 2.58 | 0.39 |
| Ti | 0.41 | — | — |
| Cr | 27.85 | 21.15 | 21.50 |
| Co | 31.35 | 3.86 | — |

TABLE 1-continued

| | Analyses | | |
|---|---|---|---|
| | | Alloys | |
| Elements | HR 160 | 230 | 800H |
| Ni | 38.11 | 55.14 | 31.75 |
| Fe | 0.49 | 2.28 | 43.40 |
| W | — | 14.04 | — |
| Mo | — | 0.96 | — |
| Mn | — | — | 1.17 |
| Cu | — | — | 0.10 |
| Al | — | — | 0.48 |

During the bench scale studies a quartz sample and a sample of each alloy were separately subjected to furnace pyrolysis conditions; these were performed under the same outlet pressure and temperature, however the ethane conversion rates and the contact times varied somewhat. These results are tabulated in Table 2.

TABLE 2

Pyrolysis Bench Test Results

| Run No. | 1 | 2 | 3 | 4 | 5 | 6 | 7 | 8 | 9 | 10 |
|---|---|---|---|---|---|---|---|---|---|---|
| Reactor | Quartz | 230 | 230 | 230 | HR160 | HR160 | HR160 | 800H | 800H | 800H |
| Contact Time(sel) | 0.17 | 0.17 | 0.17 | 0.17 | 0.16 | 0.16 | 0.16 | 0.14 | 0.15 | 0.15 |
| T, Outlet (° F.) | 1675 | 1675 | 1675 | 1675 | 1675 | 1675 | 1675 | 1675 | 1675 | 1675 |
| P, Outlet (psig) | 12 | 12 | 12 | 12 | 12 | 12 | 12 | 12 | 12 | 12 |
| Ethane Conversion, % | 61.9 | 68.4 | 70.8 | 73.3 | 75.3 | 76.9 | 75.8 | 78.1 | 80.4 | 76.8 |
| S Level, ppm | 100 | 100 | 100 | 100 | 100 | 100 | 100 | 100 | 100 | 1000 |
| CO, Mol % | 0 | 0.04 | 0.03 | 0 | 0 | 0 | 0 | 5.7 | 7.4 | 0.36 |
| Coking Rate, mg/min | 1.43 | 13.1 | 8.84 | 5.41 | 0.67 | 0.54 | 0.50 | 3.67 | 1.97 | 12.2 |

The test results indicate that HR160 has a coking rate significantly lower than that of the other alloys examined, from 3 to 26 times lower. All three alloys contained amounts of known coking elements, i.e. nickel and either iron or cobalt, however it was surprising that HR160 exhibited lower coking rates than the other alloys since it contained a significantly greater amount of cobalt which would normally be considered as a coking catalyst. More surprising is the coking ratio between HR160 and quartz; it is well known that quartz has an inherently low coking rate, and yet HR160 had a coking rate 2–3 times lower than quartz, indicating that HR160 is very inactive regarding coke formation.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

I claim:

1. In the method for reducing coking rates when cracking a hydrocarbon feedstock comprising passing the feedstock through tubes running through a furnace at an elevated temperature, the improvement wherein the tubes comprise a nickel-cobalt-chrome-silicon alloy containing:

nickel;
27.0–33.0 weight percent cobalt;
26.0–30.0 weight percent chromium;
2.4–3.0 weight percent silicon;
0.20–0.80 weight percent titanium;

not more than 3.5 weight percent iron;
not more than 1.5 weight percent manganese;
not more than 1.0 weight percent columbium;
not more than 1.0 weight percent molybdenum;
not more than 1.0 weight percent tungsten;
not more than 0.15 weight percent carbon;
not more than 0.030 weight percent phosphorus; and,
not more than 0.015 weight percent sulfur.

2. The improvement as described in claim 1, where the feedstock comprises ethane.

3. The improvement as described in claim 1, where the feedstock comprises naphtha.

4. The improvement as described in claim 1, where the elevated temperature ranges from approximately 750° C. to 1100° C.

5. The improvement of claim 1, wherein a residence time of the hydrocarbon feedstock in the furnace is approximately 0.05 to 0.6 seconds.

6. The improvement of claim 1, wherein the alloy contains less than 1 weight percent iron.

7. The improvement of claim 1, wherein the alloy contains about 0.5 weight percent iron.

* * * * *